US012606789B2

(12) United States Patent
Wang et al.

(10) Patent No.: US 12,606,789 B2
(45) Date of Patent: Apr. 21, 2026

(54) PERFUSION SYSTEMS AND CELL CULTIVATION PERFUSION SYSTEMS

(71) Applicant: SHANGHAI RUIYU BIOTECH CO., LTD., Shanghai (CN)

(72) Inventors: Xuan Wang, Shanghai (CN); Ning Li, Shanghai (CN); Rui Chen, Shanghai (CN)

(73) Assignee: SHANGHAI RUIYU BIOTECH CO., LTD., Shanghai (CN)

( * ) Notice: Subject to any disclaimer, the term of this patent is extended or adjusted under 35 U.S.C. 154(b) by 685 days.

(21) Appl. No.: 18/063,653

(22) Filed: Dec. 8, 2022

(65) Prior Publication Data

US 2023/0174914 A1      Jun. 8, 2023

(30) Foreign Application Priority Data

Dec. 8, 2021    (CN) .......................... 202111491234.7

(51) Int. Cl.
C12M 1/00        (2006.01)
C12M 1/36        (2006.01)
(52) U.S. Cl.
CPC ............ C12M 29/10 (2013.01); C12M 29/12 (2013.01); C12M 41/48 (2013.01)
(58) Field of Classification Search
CPC ....... C12M 29/10; C12M 29/12; C12M 41/48
See application file for complete search history.

(56) References Cited

U.S. PATENT DOCUMENTS

2006/0228240 A1* 10/2006 Schroeder ........... F04B 43/1223
                                                              417/476
2007/0048859 A1   3/2007 Sears
2013/0266929 A1* 10/2013 Corso ................... C12M 41/00
                                                              435/286.5
(Continued)

FOREIGN PATENT DOCUMENTS

CN        104121172 B    8/2016
CN        108260840 A    7/2018
CN        112875630 A    6/2021
(Continued)

OTHER PUBLICATIONS

Machine Translation of FR 2559214A1 (Year: 2025).*
(Continued)

*Primary Examiner* — Michael L Hobbs
(74) *Attorney, Agent, or Firm* — METIS IP LLC

(57) ABSTRACT
The present disclosure provides a perfusion system and a cell cultivation perfusion system, the perfusion system comprising: a pressure transfer component, the pressure transfer component including a belt and multiple pressure members disposed on the belt at intervals; a driving device, a driving connection being established between the driving device and the pressure transfer component; and at least one pipeline assembly, the at least one pipeline assembly including at least one pressable pipeline for fluid flow; wherein a press area is formed between the pressure transfer component and each of the at least one pressable pipeline, the multiple pressure members move with the belt, and at least a portion of the multiple pressure members press against the at least one pressable pipeline in the press area.

19 Claims, 6 Drawing Sheets

(56) References Cited

U.S. PATENT DOCUMENTS

| 2017/0253849 A1 | 9/2017 | Miller |
| 2018/0149152 A1 | 5/2018 | Asai et al. |

FOREIGN PATENT DOCUMENTS

| FR | 2559214 A1 * | 8/1985 | .......... F04B 43/1223 |
| WO | 2016030868 A2 | 3/2016 | |

OTHER PUBLICATIONS

The Extended European Search Report in European Application No. 22211895.2 mailed on May 15, 2023, 6 pages.
"The working principle and advantages and disadvantages analysis of peristaltic pump", Web page <https://www.18show.cn/zt332463/18show_Article_11506245.html>, 2017.
"How Peristaltic Pumps Work", Web page <https://www.chem17.com/st347108/Article_1276176.html>, Jun. 7, 2017.
"Reagent enclosed flow system", Web page <http://www.takasago-elec.com.cn/products/pi/>, 2016.

* cited by examiner

110

PERFUSION SYSTEMS AND CELL CULTIVATION PERFUSION SYSTEMS

CROSS-REFERENCE TO RELATED APPLICATIONS

This application claims priority of Chinese Patent Application No. 202111491234.7, filed on Dec. 8, 2021, the contents of which are incorporated herein by reference in their entirety.

TECHNICAL FIELD

The present disclosure relates to the field of peristaltic pumps and cell cultivation technology, and in particular to a perfusion system and a cell cultivation perfusion system.

BACKGROUND

A peristaltic pump is a new type of industrial pump. The peristaltic pump includes a pump head and a hose. The peristaltic pump pumps a fluid by alternately pressing and releasing the pump head against a hose. The medium transferred by the peristaltic pump does not contact the pump head, which allows pollution-free and sterile transfer, and allows the transfer of mediums that are corrosive to metal. The cleaning and disassembling of the peristaltic pump are simple and fast. The speed and flow rate of the peristaltic pump are also controllable. Therefore, the peristaltic pump is widely used in experimental research, biopharmaceuticals, analytical instruments, the medical industry, the food industry, the chemical industry, and other industries.

Taking cell cultivation perfusion as an example, in cell cultivation perfusion, the peristaltic pump may be used to transport various nutrient fluid, export waste liquid, etc. When the traditional peristaltic pump is used, the hose needs to be fixed between the pump housing and the rotor of the pump head through operations of connecting the hose, clamping the hose, and disconnecting the hose, which makes it inconvenient. For traditional multi-channel peristaltic pumps, the pumping speed for each channel is equal, and different speeds for multiple channels are not applicable. When applied in a high throughput perfusion system, if the speed control requirement for the transfer of a liquid by each pipeline is different, it is needed to provide the perfusion system with a corresponding peristaltic pump for each pipeline for individual control. This makes the whole perfusion system relatively large and complex. The assembly of the perfusion system and the maintaining of the operation of the perfusion system becomes difficult and costly. Therefore, it is desired to provide a new type of peristaltic pump system with simple assembly and easy operations which allows independent speed control of channels in both single-channel application scenarios and multi-channel application scenarios, and is suitable for building a high-throughput perfusion system.

SUMMARY

One embodiment of the present disclosure provides a perfusion system comprising: a pressure transfer component, the pressure transfer component including a belt and multiple pressure members disposed on the belt at intervals; a driving device, a driving connection being established between the driving device and the pressure transfer component; and at least one pipeline assembly, the at least one pipeline assembly including at least one pressable pipeline configured for fluid passage; wherein a press area is formed between the pressure transfer component and each of the at least one pressable pipeline, the multiple pressure members move with the belt, and at least a portion of the multiple pressure members press against the at least one pressable pipeline when moving in the press area.

In some embodiments, in the press area, there is only one press position formed through pressing a pressable section of the at least one pressable pipeline by a same pressing member of the multiple pressing members.

In some embodiments, the at least one pipeline assembly includes multiple pipeline assemblies.

In some embodiments, the at least one pipeline assembly includes multiple pressable pipelines, liquid inlet ends of the multiple pressable pipelines being connected to different liquid storage containers, and liquid outlet ends of the multiple pressable pipelines being connected to a same target container.

In some embodiments, the at least one pipeline assembly includes multiple pressable pipelines, liquid inlet ends of the multiple pressable pipelines being connected to a same liquid storage container, and liquid outlet ends of the multiple pressable pipelines being connected to different target containers.

In some embodiments, in the press area, a pressable section of each of the at least one pressable pipeline is simultaneously pressed by adjacent pressure members of the multiple pressure members, thereby forming a blocked fluid section, wherein when the at least one pressable pipeline include multiple pressable pipelines, and the at least a portion of the multiple pressure members press the multiple pressable pipelines within the press area, a length of the blocked fluid section of one or more of the multiple pressable pipelines is greater than a distance between the adjacent pressure members.

In some embodiments, the multiple pressure members move in a straight line in the press area.

In some embodiments, when the at least one pipeline assembly includes multiple pipeline assemblies and the at least one pressable pipeline includes multiple pipelines, pressable sections of the multiple pressable pipelines of the multiple pipeline assemblies are disposed at intervals along a straight line of a movement of the multiple pressed members.

In some embodiments, when the at least one pressable pipeline includes multiple pressable pipelines: pressable sections of the multiple pressable pipelines are disposed at intervals along a straight line of a movement of the multiple pressure members; or pressable sections of the multiple pressable pipelines are disposed side by side in a direction that is perpendicular to a straight line of a movement of the multiple pressure members and parallel to a working plane of the belt in the press area.

In some embodiments, a pressable section of one or more of the at least one pressable pipeline is a straight-line section, a folded-line section, or a curved section.

In some embodiments, when the pressable section is a straight-line section, the straight-line section is arranged such that an angle between the straight-line section and the straight line of a movement of the multiple pressure members ranges from 0-89°.

In some embodiments, within the press area, the section of the at least one pressable pipeline is simultaneously pressed by adjacent pressure members, thereby forming a blocked fluid section, wherein the blocked fluid section moves with a movement of the pressed member, a length of the blocked fluid section being less than or equal to a length of the blocked fluid section after a movement.

In some embodiments, the perfusion system further includes a support section, the at least one pipeline assembly being placed on a pressure-bearing surface of the support section, a pressable section of each of the at least one pressable pipeline being located between the pressure-bearing surface and the pressure transfer component.

In some embodiments, when the pressure-bearing surface is horizontal, a ratio of a horizontal projected area of the press area to a horizontal projected area of the pressure transfer component is greater than 70%.

In some embodiments, the perfusion system is an integrated perfusion system, wherein the integrated perfusion system includes a main body, the main body having a protrusion component, the pressable section of each of the at least one pressable pipeline is provided within the protrusion component, wherein the protrusion component is placed between the pressure-bearing surface and the pressure transfer component, and the protrusion component is configured to cooperate in pressing the at least one pressable pipeline.

In some embodiments, when the pressure-bearing surface is horizontal, a ratio of a horizontal projected area of the protrusion component to a horizontal projected area of the main body is less than 25%.

In some embodiments, in the press area, at least two of the multiple pressure members simultaneously press on each of the at least one pressable pipeline.

In some embodiments, the multiple pressure members on the belt are equally spaced from each other; and a distance between adjacent pressure members of the multiple pressure members is 0.5-100 mm.

In some embodiments, the multiple pressure members are rollers, each of the rollers being rotatably connected to the belt.

In some embodiments, the belt includes multiple links sequentially connected in a loop, wherein each of the multiple links includes a connecting shaft and a connecting plate installed at both ends of the connecting shaft, the connecting plates of adjacent links being rotatably connected.

One embodiment of the present disclosure provides a cell cultivation perfusion system comprising a cell incubator, said cell incubator being provided with either a peristaltic pump device as described above or a peristaltic pump system as described above.

BRIEF DESCRIPTION OF THE DRAWINGS

This description will be further explained in the form of exemplary embodiments, which will be described in detail by means of accompanying drawings. These embodiments are not restrictive, in which the same numbering indicates the same structure, wherein.

Figure 1:
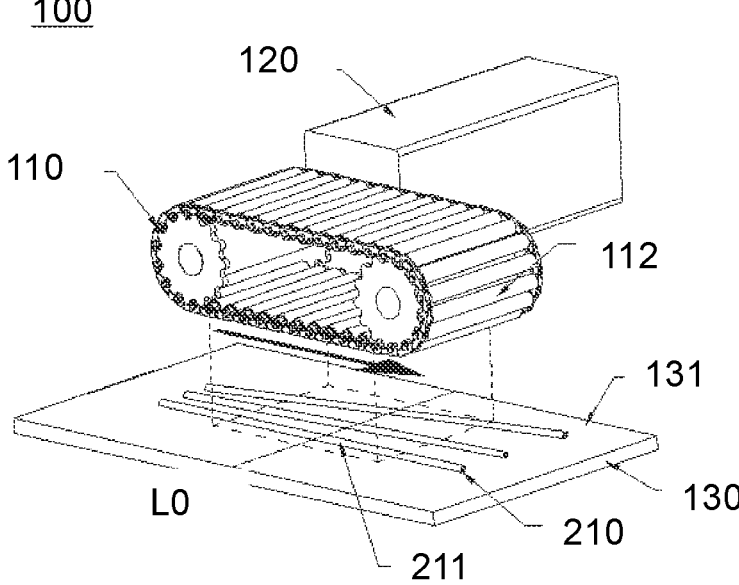
FIG. 1 is a schematic diagram illustrating an exemplary application scenario of a perfusion system according to some embodiments of the present disclosure.

Marks in the drawings: 100—perfusion system; 110—pressure transfer component; 111—belt; 112,112a, 112b,112c, and 112d—pressure member; 113—driving wheel; 114—driven wheel; 115—support plate; 1111—connecting plate; 1111a—insertion member; 1111b—adapter; 1111c—toothed protrusion; 1112—connecting shaft; 120—driving device; 130—support section; 131—pressure-bearing surface; 200—integrated perfusion system; 210—pressable pipeline; 211, 211a, 211b, 211c, and 211d—pressable section; 2111—diameter-varying section; 2112—non-diameter-varying section; 212, 213, 214—non-pressing sections; 215—fluid storage chamber; 216—target chamber; 217—waste fluid chamber; 220—main body; 220a— protrusion component; 224—cover.

DETAILED DESCRIPTION

Exemplary embodiments or implementations will be described in detail herein, examples of which are represented in the accompanying drawings. Where the following description relates to the accompanying drawings, unless otherwise indicated, the same numerals in different accompanying drawings indicate the same or similar elements. The embodiments described in the following exemplary embodiments do not represent all embodiments consistent with the present disclosure. Rather, they are only examples of devices and methods that are consistent with some aspects of the present disclosure as detailed in the appended claims.

The terms used in this present disclosure are used solely for the purpose of describing particular embodiments and are not intended to limit this present disclosure. The singular forms of "a," "the," and "that" as used in this present disclosure and the appended claims are also intended to include most forms, unless the context clearly indicates otherwise.

It should be understood that the terms "first," "second" and similar terms used in the specification and claims of this application do not indicate any order, number, or importance, but are used only to distinguish the different components. Similarly, similar words such as "a" or "one" do not indicate a limit to the number of words, but rather the existence of at least one. Unless otherwise noted, the terms "front," "rear," "lower," and/or "upper" and similar terms are for illustrative purposes only and are not limited to a location or a spatial orientation. Similar words such as "including" or "comprising" are intended to mean that the elements or objects that appear before "including" or "comprising" cover the elements or objects that appear after "including" or "comprising" and their equivalents, and do not exclude other elements or objects.

In some embodiments, the peristaltic pump includes a rotor-type pump head and a pump body. The peristaltic pump pumps a fluid by alternately pressing and releasing the pump head against a hose. This peristaltic pump needs to pre-shape the hose, that is, the hose needs to be fixed in the pump head between a pump housing and a rotor so as to pump the fluid. The pre-shaping needs connecting, clamping, and disconnecting the hose, which is cumbersome and inconvenient. Moreover, in this peristaltic pump structure, the structure of the pump head pressing the hose occupies more space and has low space utilization, which is not suitable for application in a cell cultivation perfusion system where space is limited. In addition, the existing peristaltic pump may not achieve different velocities for multi-channel fluid pumping. When the existing peristaltic pump is applied to a complex high-throughput cell cultivation perfusion system, the use of multiple peristaltic pumps for cooperation is needed, which causes the fact that the entire cell cultivation perfusion system is too large, and the fact that the cost of building and maintaining the cell cultivation perfusion system is high.

Some embodiments of this specification provide a perfusion system 100. A pressure transfer component 110 of the perfusion system 100 uses a belt structure, and the belt-type pressure transfer component 110 may perform pressure pumping for a variety of pipeline assemblies with different arrangements. The pipeline assembly and the pressure transfer component 110 may be quickly assembled and separated via convenient operations. At the same time, the belt structure of the pressure transfer component 110 allows high space utilization in its press area, thus allowing the perfusion system 100 to reserve sufficient space for other application needs, such as optical detection. Alternatively, the perfusion system 100 may perform a pumping for a single pressed pipeline of a single-pipeline assembly with controllable pump speed; the perfusion system 100 may also perform a multi-channel pumping for multiple pressable pipelines of a multi-pipeline assembly; and different velocities for multi-channel fluid pumping may be achieved through different cooperations between the pressable pipeline and the pressure transfer component 110.

The perfusion system 100 and peristaltic pump system involved in the embodiments of this present disclosure will be described in detail below in conjunction with FIGS. 1-12. It should be noted that the following embodiments are used only to explain the present disclosure and do not constitute a limitation of the present disclosure.

Referring to FIG. 1, FIG. 1 is a schematic diagram illustrating an exemplary application scenario of a perfusion system according to some embodiments of the present disclosure. In some embodiments, the perfusion system 100 includes a pressure transfer component 110, a driving device 120, and a pipeline assembly. The pipeline assembly provides a channel for the fluid to flow and be transported. A driving connection is established between the driving device 120 and the pressure transfer component 110 for providing power to the pressure transfer component 110 for pressing. The pressure transfer component 110 is used to press the pipeline assembly to achieve the pumping of the fluid.

Figure 2:
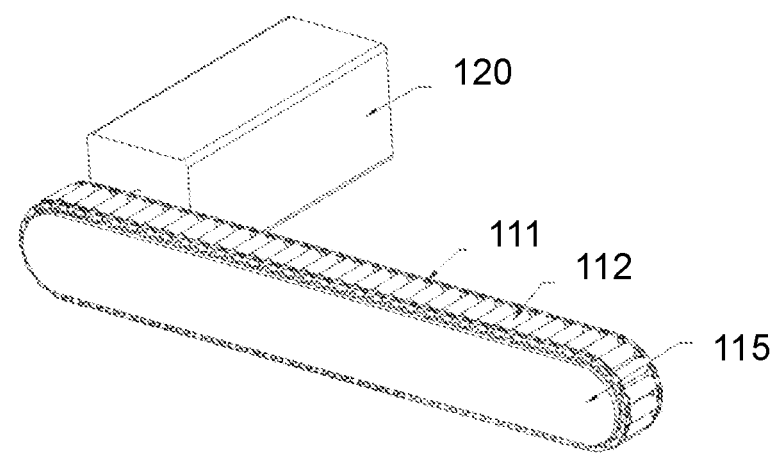
FIG. 2 is a schematic diagram illustrating an exemplary assembly of a pressure transfer component and a driving device according to some embodiments of the present disclosure.
Figure 3:
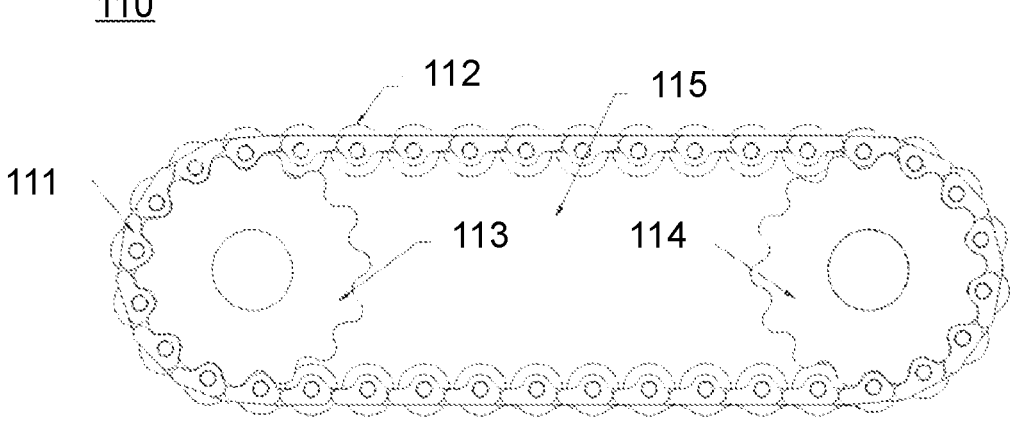
FIG. 3 is a schematic diagram illustrating an exemplary structure of a pressure transfer component according to some embodiments of the present disclosure.

Referring to FIG. 2 and FIG. 3, FIG. 2 is a schematic diagram illustrating an exemplary assembly of the pressure transfer component 110 and the driving device 120 according to some embodiments of the present disclosure; FIG. 3 is a schematic diagram illustrating an exemplary structure of the pressure transfer component 110 according to some embodiments of the present disclosure. In some embodiments, the pressure transfer component 110 includes a belt 111 as well as multiple pressure members 112 disposed on the belt 111 at intervals. The belt 111 is connected to the driving device 120 by transmission, and the belt 111 is powered by the driving device 120 for operation. With the operation of the belt 111, the pressure member 112 protruding from the belt 111 may contact the pipeline assembly and thus press the pipeline assembly, thus realizing the pumping of liquid.

Figure 4:
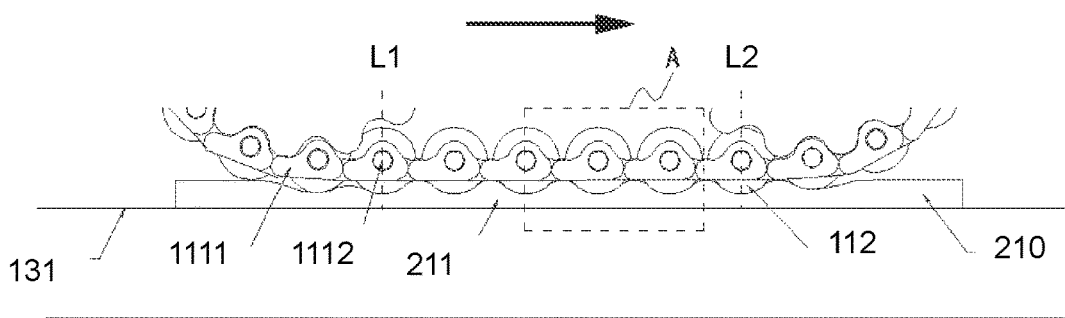
FIG. 4 is a schematic diagram illustrating an exemplary structure when a pressure transfer component presses a pipeline assembly according to some embodiments of the present disclosure.

FIG. 4 is a schematic diagram illustrating an exemplary structure when the pressure transfer component 110 presses the pipeline assembly according to some embodiments of the present disclosure. In some embodiments, the pipeline assembly includes a pressable pipeline 210 for fluid passage, and the pressure transfer component 110 and the pipeline assembly between the pressable pipeline 210 to form a press area. The press area is an area where continuous contact between the pressable pipeline 210 and the pressure transfer component 110 forms the pressure therebetween. The pressing movement path of each pressure member 112 passes through the press area. The pressing movement path of each pressure member 112 is the movement path of the pressure member 112 from the start of pressing the pressable section 211 of the pressable pipeline 210, which is configured to block the press area of the pressable section 211, to the end of pressing, which is configured to unblock the press area of the pressable section 211. For example, the press area in FIG. 4 may be the area between the dashed line L1 and the dashed line L2. The pressable section 211 may be the entire section of the pressable pipeline 210, or it may be a portion of the section of the pressable pipeline 210. For example, the pressable section 211 of the pressable pipeline in FIG. 4 is substantially the section of the pressable pipeline 210 between the dashed line L1 and the dashed line L2.

Figure 5:
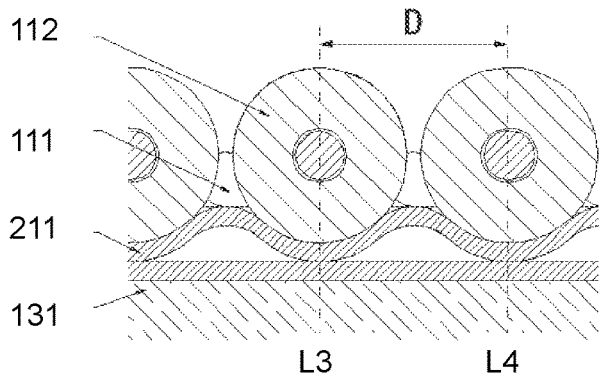
FIG. 5 is an exemplary sectional diagram illustrating when a pressure transfer component is pressed according to some embodiments of the present disclosure.

FIG. 5 is a cross-sectional diagram at A in FIG. 4. As shown in FIG. 5, in the press area, the pressure surface of the pressure member 112 continuously pushes and blocks the pressable pipeline, and the simultaneous pressing of two adjacent pressure members 112 causes the pressable section 211 to form a blocked fluid section. The blocked fluid section is a pipeline in which the pressable section 211 is pressed by the adjacent pressure member 112 and is in a blocked state. For example, the blocked fluid section in FIG. 5 may be a pipeline located between the dashed line L3 and the dashed line L4. The pressure member 112 pushes the pillow-shaped fluid within this blocked fluid section, causing the pillow-shaped fluid to flow within the pressable section 211.

The direction of the inflow and outflow of the fluid in the pressable section 211 of the pressable pipeline 210 matches the direction of pressing of the pressure member 112. The belt 111 is an annular belt structure, and the outer contour surface of the belt 111 is the working plane of the belt 111. The entire working plane of the belt 111 may be considered as a column surface formed by a straight-line moving parallelly along a planar curve; the straight-line is the generatrix of the column surface (working plane); the planar curve is the directrix of the column surface (working plane); the generatrix is perpendicular to the plane where the directrix is located. The pressing direction of the pressure member 112 may be in the direction of movement of a portion of the section along the working plane alignment of the belt 111. In some embodiments, in the press area, at any given moment, there is only one press position formed through pressing the pressable section 211 of the pressable pipeline 210 by the same pressure member 112, so that the direction of the inflow and outflow of the fluid in the pressable section 211 and the pressing direction of the pressure member 112 match, and the fluid in the pressable section 211 may flow normally. When there are two or more press positions formed through pressing the pressable section 211 of the pressable pipeline 210 by the same pressure member 112, the directions of the fluid flow at two ends of the pressable section 211 between adjacent press positions are opposite, and thus the fluid may not flow properly. As shown in FIG. 4, from the direction of the working plane generatrix of the belt 111 (front view angle), the inlet end of the pressable section 211 is near the beginning of the pressing movement path of the pressure member 112, and the outlet end of the pressable section 211 is near the end of the pressing movement path of the pressure member 112. There is only one press position between each pressure member 112 and the pressable section 211, so that the fluid inflow and outflow direction of the pressable section 211 matches the pressing direction of the pressure member 112.

In some embodiments, the pressure member 112 moves in a straight line within the press area. As shown in FIG. 4, during the pressing of the pipeline assembly by the pressure transfer component 110, the belt 111 running in a loop drives the pressure member 112 into the press area from the left side. The working plane of the belt 111 in the press area is a plane formed by the generatrix moving parallel to a straight-line segment along the directrix, and with the operation of the belt 111, the pressure members 112 as a whole move in a straight line in the direction from left to right. In some embodiments, further, in the press area, the pressable section 211 of the pressable pipeline 210 is located in a plane parallel to the working plane of the belt 111. As shown in FIG. 4, the pressable pipeline 210 as a whole is located on a plane, and the plane where the pressable pipeline 210 is located is parallel to the working plane of the belt 111 in the press area, so that each pressure member 112 presses the hose wall of the pressable section 211 with approximately the same pressure.

Figure 6:
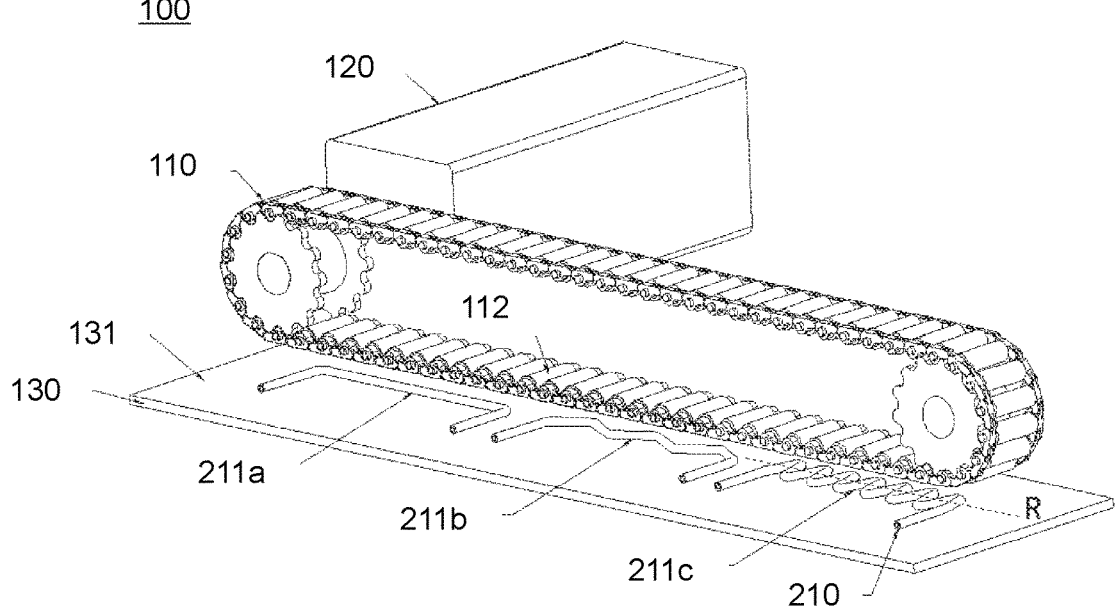
FIG. 6 is a schematic diagram illustrating an exemplary application scenario of a perfusion system according to some embodiments of the present disclosure.

The pressable section 211 may have various shapes. In some embodiments, the pressable section 211 is a straight-line section. FIG. 6 is a schematic diagram illustrating an exemplary application scenario of a perfusion system according to some embodiments of the present disclosure. As shown in FIG. 6, the pressable section 211a is a straight-line section, and the pressure member 112 of the pressure transfer component 110 moves in a straight line within the press area, with the pressable section 211a parallel to the movement of the pressure member 112 in a straight line. The position relationship between the straight-line section and the movement path of the pressure member 112 affects the pumping speed of the corresponding pressable pipeline 210.

In some embodiments, the pressable section 211 is a folded-line section. For example, the folded-line section may be W-shaped. As shown in FIG. 6, the pressable section 211b is a folded-line section, and the pressure member 112 of the pressure transfer component 110 moves in a straight line in the press area, and the sections of the pressable section 211a have equal angles to the straight-line of a movement of the pressure member 112. In some embodiments, the pressable section is curved. For example, the curved section may take the form of a trigonometric curve. As shown in FIG. 6, the pressable section 211c is a curved section that has a substantially sinusoidal shape. The pressable section 211c varies periodically along the transverse axis R, and the pressure member 112 of the pressure transfer component 110 moves in a straight line in the press area. The transverse axis R of the pressable section 211c with the sinusoidal shape is parallel to the straight line of the movement of the pressure member 112.

In some embodiments, when the pressable section 211 is a straight-line section, the straight-line section is arranged such that an angle between the straight-line section and the straight line of a movement of the pressure member 112 ranges from 0-89°. When distances between adjacent pressure members of the multiple pressure members are equal, velocities of the pressure members are equal, and a cross-sectional area of the at least one pressable pipeline is invariable, a pumping speed of the straight-line section when the straight-line section is parallel to the straight line of a movement of the multiple pressure members is less than a pumping speed of the straight-line section when there is an acute angle between the straight-line section and the straight line of the movement of the multiple pressure members. In some embodiments, when the pressable section is a straight-line section, the straight-line section is at an angle of 0 to 45° to the straight line of movement of the pressing.

In the case of different pressure members 112 and press area settings, the blocked fluid section formed by the pressure on the pressable section 211 has different movement features. In the case where the distance between adjacent pressure members 112 is equal to the length of the pressing movement path of pressure members 112 in the press area, when a previous pressure member 112 moves to the end of its pressing path, and a rear pressure member 112 moves to the beginning of its pressing path, the adjacent pressure members 112 simultaneously press the pressable section 211 of the pressable pipeline 210. Thus, the pressable section 211 is pressed to form a blocked fluid section, and the blocked fluid section is the initial blocked fluid section. As the previous pressure member 112 leaves the press area and ends its pressing movement path, the initial blocked fluid section described above disappears and the blocked fluid section does not move with the pressure member movement. In the case where the distance between adjacent pressure members 112 is less than the length of the pressing movement path of the pressure member 112 in the press area, the movement of the rear pressure member 112 to the start of its pressing movement path causes the previous pressure member 112 and the rear pressure member 112 to press in the pressable section 211 between them, thereby forming an initial blocking fluid segment; the two pressure members 112 move with the belt 111, and the blocked fluid section formed by the pressing of the two pressure members 112 may move with the movement of the pressure members 112.

For different shapes of the pressable section 211, the length of the blocked fluid section 211 formed by the pressure on the pressable section 211 varies during the movement with the pressure member 112. It should be noted that the length of the blocked fluid section is the length of the pressable pipeline section 211 pressed by the adjacent pressure member 112 and in the blocked state. In some embodiments, when the blocking fluid segment formed by the pressure on the pressable section 211 moves with the pressure member 112, the length of the initial blocked fluid section is less than or equal to the length of the blocked fluid section after moving.

Figure 7:
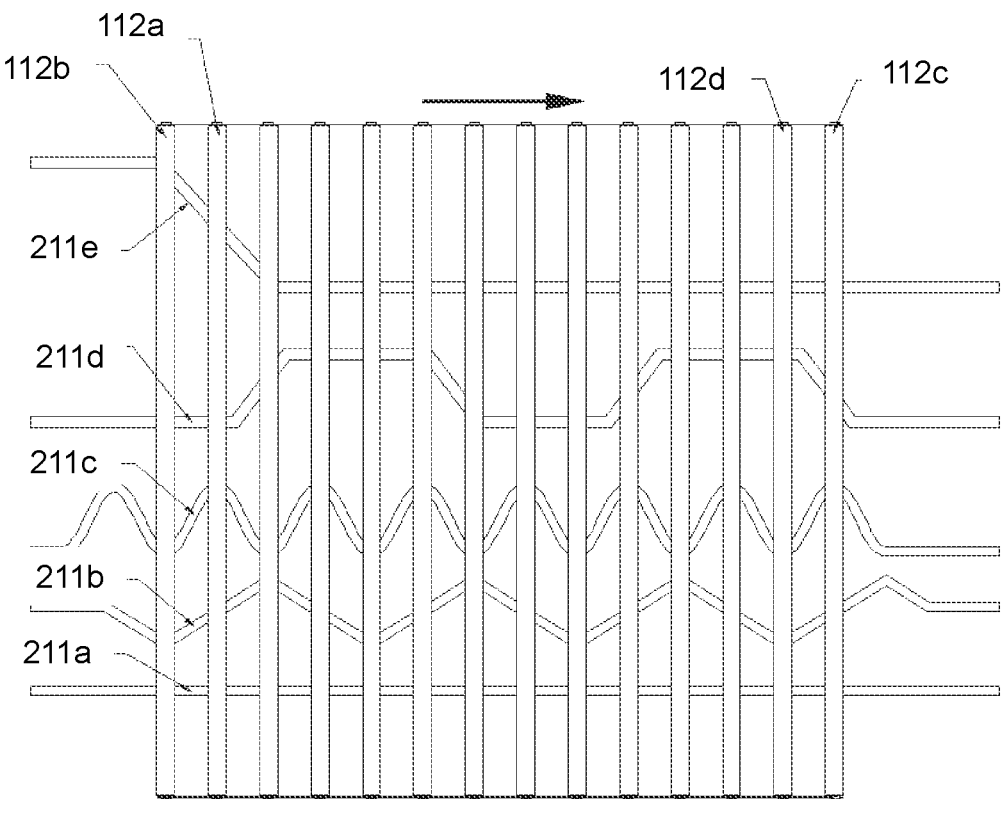
FIG. 7 is a schematic diagram illustrating an exemplary structure of the perfusion system when a pressure transfer component presses different pressable sections in a press area according to some embodiments of the present disclosure.
Figure 8:
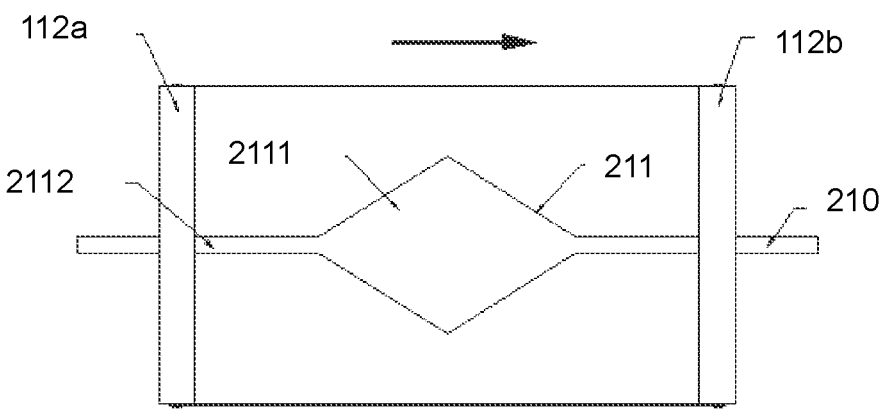
FIG. 8 is a schematic diagram illustrating an exemplary structure of a pressure transfer component in a press area when pressing a pressable pipeline including a diameter-varying section, according to some embodiments of the present disclosure.

The variation in length of the different blocked fluid sections 211 is illustrated with reference to FIG. 7, which is a schematic diagram illustrating an exemplary structure when the pressure transfer component presses different pressable sections in the press area according to some embodiments of the present disclosure. When the pressable section 211 is a curved section or a folded-line section, with the movement of the pressure member 112, the length of the blocked fluid section after moving may be different from the initial length of the blocked fluid section, and because the ends of the blocked fluid section are in a blocked state, the fluid cannot be circulated, so the volume of the fluid remaining in the blocked fluid section remains the same. As shown in FIG. 7, the press area may be located between the pressure members 112b to 112c when viewed from a top perspective. In the press area, the pressure member 112b is located at the initial position of its pressing movement path, and the pressure member 112c is located at the final position of its pressing movement path, and the pressure members 112a, 112b, and 112d of the pressure transfer component 110 move in a straight-line from left to right to press the pressable sections 211a, 211b, 211c, and 211d simultaneously by the pressure member 112b and the adjacent pressure member 112a, so that each of the pressable sections 211a, 211b, 211c, and 211d forms an initial blocked fluid section. The pressable section 211e, is a folded-line section. For the pressable section 211e, the length of the initial blocked fluid section between the pressure member 112a and the pressure member 112b is equal to the length of the line between the pressure member 112a and the pressure member 112b, and when the pressure member 112a moves to the position of the pressure member 112c, the length of the blocked fluid section between the pressure member 112a and the pressure member 112b after moving is less than the length of its initial blocked fluid section. When the length of the blocked fluid section after moving is less than the initial length of the blocked fluid section, the retained fluid may cause the length of the corresponding blocked fluid section to shorten after the movement of the pipeline expansion. The length of the initial blocked fluid section is less than or equal to the length of the blocked fluid section after moving, which may avoid the above-mentioned phenomenon of pipeline expansion and reduce the local deformation caused by the long-time expansion of the pipeline.

Though the shape arrangement of the pressable section 211 and the way the position of the pressable section 211 fits with the pressure member 112 in the press area, the length of the initial blocked fluid section corresponding to the pressable section 211 may be changed to be less than or equal to the length of the blocked fluid section after moving. As shown in FIG. 7, the pressable section 211a is a straight-line section with an initial blocked fluid section having a length equal to the distance between the pressure member 112a and the pressure member 112b; for the pressable section 211a, the length of the blocked fluid section after moving is always equal to the length of the initial blocked fluid section. The pressable section 211b is a W-shaped folded-line section, the segments of the folded-line section are of equal length and each section forms an equal angle with the straight-line of movement of the pressure member 112, and the length of its initial blocked fluid section is equal to half the length of the section; for the pressable section 211b, the length of the blocked fluid section after moving is always equal to the length of the initial blocked fluid section. The pressable section 211c is a curved section in the form of a sine wave, and the length of the initial blocked fluid section is the chord length of half a cycle, and for the pressable section 211c, the length of the blocked fluid section after moving is always equal to the length of the initial blocked fluid section. The pressable section 211d is a folded-straight-line section with two adjacent sections having different angles with respect to the straight lines of movement of the pressure member 112a and the pressure member 112b, and the initial blocked fluid section of the pressable section 211d and the pressable section 211b are of equal length; for the pressable section 211, the length of the blocked fluid section after moving is always greater than or equal to the length of the initial blocked fluid section.

The perfusion system 100 may perform a single-channel pumping of a fluid for a single pipeline assembly for single-channel fluid pumping. In some embodiments, the perfusion system 100 may be a pipeline assembly, and the pipeline assembly includes a pressable pipeline 210. The perfusion system 100 may control the speed of movement of the pressure member 112 through the driving device, thereby controlling the speed of the pumping of the fluid in the individual pipeline assembly.

The perfusion system 100 may target multiple pipeline assemblies for multi-channel fluid pumping. In some embodiments, the perfusion system 100 may include multiple pipeline assemblies, and the multiple pipeline assemblies may be used to perform multiple identical or different perfusion operations in the meantime. For example, the perfusion system 100 in FIG. 6 is set up with three pipeline assemblies, and the pressure transfer component 120 simultaneously presses the pressable pipeline 210 of the three pipeline assemblies, thus achieving multi-channel fluid pumping. The count of pipeline assemblies in the perfusion system 100 may be configured according to the needs of the actual application, and this embodiment is not limited. To optimize the space utilization of the press area of the perfusion system 100, in some embodiments, when the perfusion system 100 includes multiple pipeline assemblies, the pressable section 211 of the pressable pipeline 210 of different pipeline assemblies is spaced in the direction of movement of the pressure member 112. As shown in FIG. 6, in the press area, the pressure member 112 moves in a straight line, and the three pipeline assemblies are arranged in a plane parallel to the working plane of the belt 111 in the press area, and the pressable sections 211a, 211b, and 211c of the different pipeline assemblies are arranged at intervals along the straight-line of the movement of the pressure member 112.

The perfusion system 100 may be used for multi-channel fluid pumping for pipeline assemblies containing multiple pressable pipelines 210. In some embodiments, the pipeline assembly includes a liquid storage container and multiple target containers; each target container is connected to the liquid storage container through a corresponding pressable pipeline 210, and multiple pressable pipelines 210 of the pipeline assembly are connected in parallel. In some embodiments, the pipeline assembly includes a target container and multiple liquid storage containers, each liquid storage container is connected to a liquid storage container through a corresponding pressable pipeline 210, and multiple pressable pipelines 210 of the pipeline assembly are connected in parallel.

The multiple pressable pipelines 210 of the same pipeline assembly may be arranged in a variety of ways within the press area. In some embodiments, the multiple pressable pipelines 210 of the same pipeline assembly may be spaced apart in the direction of movement of the pressure member 112. For example, in the press area, when the pressure member 112 moves in a straight line, the pipeline assembly may be correspondingly arranged in a plane parallel to the working plane of the belt 111 in the press area, and multiple pressable sections 211 of the same pipeline assembly may be spaced along the straight-line of the movement of the pressure member 112. To optimize the layout of the perfusion system and the space utilization in the press area, in some embodiments, the multiple pressable pipelines 210 of the same pipeline assembly may be arranged side by side in a direction perpendicular to the straight line of the movement of the pressure member 112 and parallel to the working plane of the belt 111 in the press area. For example, as shown in FIG. 1, in the press area, the pressure member 112 moves in a straight line, and the pipeline assembly may be arranged in a plane parallel to the working plane of the belt 111 in the press area, and multiple pressable sections 211 of the same pipeline assembly may be arranged side by side in a straight-line L0, which is perpendicular to the movement line of the pressure member 112 and parallel to the working plane of the belt in the press area.

In some embodiments, when the pressure member 112 presses multiple pressable pipelines 210 in the press area, the length of the blocked fluid section of at least one of the pressable pipelines is greater than the distance between adjacent pressure members 112. In the case of equal distance between adjacent pressure members 112, equal speed of movement of pressure members 112, and equal cross-sectional area of the pressable pipeline 210, the fluid pumping speed of the pressable pipeline is slowest when the length of the initial blocked fluid section is equal to the distance between adjacent pressure members; the longer the length of the initial blocked fluid section, the faster the fluid pumping speed of the pressable pipeline 210.

Further, in some embodiments, when the pressure transfer component 110 simultaneously presses multiple pressable pipelines 210, the length of their initial blocked fluid sections is not equal in at least two of the pressable pipelines 210. For each pressable pipeline 210, when a previous pressure member 112 moves to and away from the end position of its pressing path, the previous pressure member 112 is released from the blocked state at the press position formed on the pressable section 211, and the fluid remaining in the blocked fluid section between the two pressure members 112 is pumped forward by the rear pressure member 11. The size of the volume of the fluid pumped forward per unit of time determines the speed of the pumping of the fluid. The volume of the fluid retained within the blocked fluid section remains constant during the movement of the blocked fluid section with the pressure member 112, and the volume of the fluid retained within the blocked fluid section is determined by the initial length of the blocked fluid section. Therefore, in the pressure member 112 movement speed, adjacent pressure members 112 spacing and pressable pipeline 210 cross-sectional area is equal, if the initial blocked fluid section length in the two pressable pipelines 210 is not equal, the pumping speed of the two pressable pipelines 210 is different.

In some embodiments, when the perfusion system 100 includes multiple pressable pipelines 210, the pressable sections 211 of the multiple pressable pipelines 210 are a combination of one or more of straight sections, folded-line sections, and curved sections. Specifically, in the case where the perfusion system 100 includes multiple pressable pipelines 210 for independent fluid delivery, i.e., when the perfusion system 100 includes multiple pipeline assemblies and/or each pipeline assembly includes multiple pressable pipelines 210, the length of the initial blocked fluid section in different pressable sections 210 may be controlled by the combination of the shape and position of the pressable sections 210 to achieve different velocities for multi-channel fluid pumping.

In some embodiments, the pressure transfer component 110 simultaneously presses multiple straight-line sections, with the multiple straight-line sections set at different angles to the straight line of movement of the pressure member 112 so that the multiple pressable pipelines 210 are pumped at different speeds. The perfusion system shown in FIG. 1 includes three pressable pipelines 210, the pressable section 211 of the three pressable pipelines 210 are straight-line sections. The difference is that the angle between the pressable section of the three pressable pipelines 211 and the movement of the pressure member 112 are 0°, 15°, and 30. With the increase of the above-mentioned angle, the fluid pumping speed of the three pressable pipelines 210 increases in turn. In some embodiments, the pressure transfer component 110 simultaneously presses multiple folded-line sections, each folded-line section including multiple sections where the angle between adjacent sections is the same and the angle between the multiple sections and the straight-line of movement of the pressure member 112 is the same. The sections of the multiple folded-line sections are set at different angles to the straight line of movement of the pressure member 112 to allow different pumping speeds of the multiple pressable pipelines 210. In some embodiments, the pressure transfer component 110 simultaneously presses multiple curved sections; the curved sections have a sinusoidal shape; the multiple curved sections vary periodically along a straight line parallel to the movement line of the pressure member 112; the multiple curved sections vary in the same magnitude but not in the same period; or the multiple curved sections vary in the same magnitude but not in the same period, so that the pumping speed values of the multiple pressable pipelines are different.

In some embodiments, the pressure transfer component 110 presses both a straight-line section and a folded-line section, with the straight-line section parallel to the movement line of the pressure member 112 and the folded-line section including multiple sections, with adjacent sections at the same angle and multiple sections set at an acute angle to the movement line of the pressure member 112, so that the pumping speed of the straight-line section and the folded-line section is different. In some embodiments, the pressure transfer component 110 simultaneously presses a straight-line section and a curved section. The straight-line section is parallel to the straight line of movement of the pressure member 112. The curved section has a sinusoidal shape and varies periodically along a straight line parallel to the straight line of movement of the pressure member 112. Thus, the straight-line section and the curved section have different pumping speeds. For example, the perfusion system shown in FIG. 6 includes multiple pressable pipelines 210, and the pressure transfer component 110 simultaneously presses the multiple pressable pipelines. The pressable section 211a is a straight-line section, the pressable section 211b is a folded-line section, the pressable section 211*c* is a curved section, the pumping speed of the fluid in the pressable section 211*a*, the pressable section 211*b* and the pressable section 211*c* increases in turn. The perfusion system is shown in FIG. 7 includes multiple pressable pipelines 210, and the pressure transfer component 110 simultaneously presses the multiple pressable pipelines 210. The pumping speed of the pressable section 211*a* is the slowest, the pumping speed of the pressable section 211*b* and the pressable section 211*d* is the middle, and the pumping speed of the pressable section 211*c* is the fastest.

In some embodiments, one or more of the pressable pipelines 210 of the pipeline assembly may include a diameter-varying section within the press area. The diameter-varying section is the section of the pipeline where the cross-sectional area varies continuously or discontinuously. In the press area, the pressure transfer component 110 presses the pressable pipeline 210 containing the diameter-varying section, which may cause the fluid in the pressable pipeline 110 to be in a non-uniform flow state. For example, the perfusion system 100 shown in FIG. 8 includes a pressable pipeline 210, and the pressable section 211 of the pressable pipeline 210 includes a diameter-varying section 2111 and a non-diameter-varying section 2112. The non-diameter-varying section is the section of the pipeline where the cross-sectional area remains the same. Within the press area, the pressure member 112*a* of the pressure transfer component 110 is located at the initial position of its pressing movement path, and the pressure member 112*b* is located at the end of its pressing movement path. In the press area, the adjacent pressure members 112*a*, and 112*b* move in a straight-line from left to right. After the pressure members 112*a*, and 112*b* leave the press area and end the pressing pressable section 211, the pressure member 112*a* continues to move to the right to the end of its pressing movement path (the position of the pressure member 112*b* in FIG. 8). The fluid flow speed within the pressable pipeline 210 remains constant while the pressure member 112*a* is pressing the non-diameter-varying section 2112; when the pressure member 112*a* presses the diameter-varying section 2111, the fluid flow speed in the pressable pipeline 210 is in a continuously changing state, i.e., firstly increases and then decreases. By controlling the change in cross-sectional area of the diameter-varying section 2111 of the pressable pipeline 210 and the pressing matching relationship between the pressure transfer component 110 and the pressable pipeline 210, the fluid is pumped at a non-uniform state, which may make the perfusion system 100 meet different fluid pumping requirements (such as pulse pumping).

In some embodiments, for fluid pumping, at least one pressure member 112 is present in the press area at any given time. During the working of the perfusion system 100, the pressure member 112 in the press area is in contact with the pressable pipeline 210 and forms a block in the pipeline, and as the pressure member 112 moves, the fluid in the pipeline ahead of the block is pumped forward; at this time, the rear of the blocked pipeline is a vacuum, and the fluid may be continuously inhaled from the container connected to the inlet end of the pressable pipeline. When the first pressure member 112 moves to the end of its pressing path, the next pressure member 112 moves to the beginning of its pressing path, and the next pressure member 112 takes over from the previous pressure member 112 for the next round of the pumping of the fluid.

In some embodiments, at least 2 pressure members 112 are present in the press area at any given time. The greater the count of pressure members 112 of the pressable pipeline 210, the smaller the fluid pulse of the perfusion system 100, and the smaller the flow speed fluctuations, the more accurate the pumping flow. In some embodiments, the count of pressure members 112 that simultaneously form a pressing to the pressable pipeline 210 may be 2 to 100 in the press area.

In some embodiments, the distance between adjacent pressure members 112 on the belt 111 (i.e., D in FIG. 5) is equal. Equally spaced pressure members 112 easily adapt to a variety of different shapes of the pressable section 211 for fluid pumping. In other embodiments, the distance between adjacent pressure members 112 on the belt 111 may also be set according to the actual situation, such as a large and small distance spacing or a gradually increasing distance, etc.

In some embodiments, the distance between adjacent pressure members 112 may be 0.5 to 100 mm. In some embodiments, preferably, the distance between adjacent pressure members 112 may be 1 to 10 mm.

In some embodiments, the pressure member 112 is provided in the direction of the width of the belt 111. The width of the belt 111 is oriented in a direction parallel to the generatrix of the working plane of the belt 111 in the form of a columnar surface. The longer the length of the pressure member 112 along the width of the belt 111, the larger the press area, and the more the pressure members 112 that simultaneously press the pressable pipeline 210. In some embodiments, the pressure member 112 is set in a length of 2 mm to 100 mm along the width of the belt 111.

Figure 9:
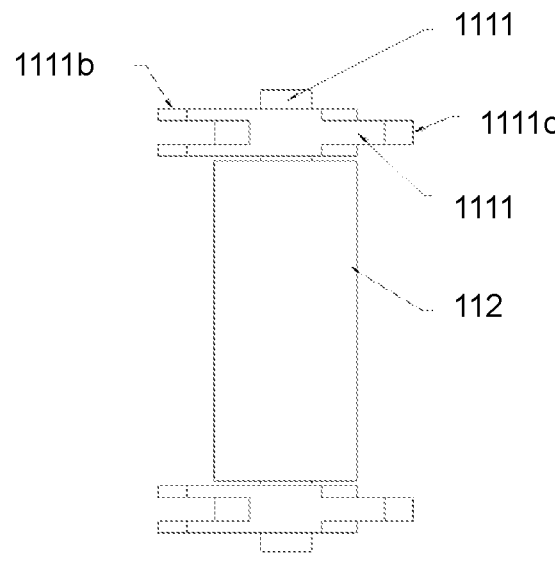
FIGS. 9 and 10 are schematic diagrams illustrating exemplary assembly of links and pressure members according to some embodiments of the present disclosure.
Figure 10:
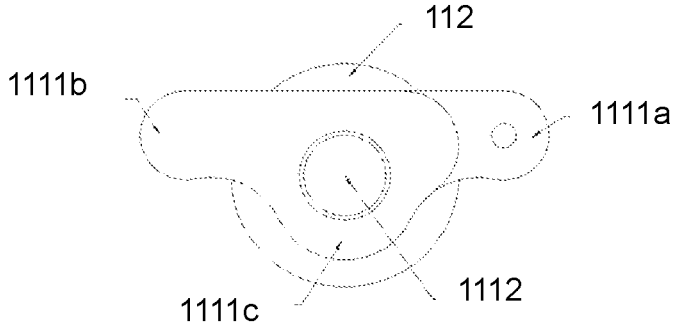

Referring to FIGS. 3 and 4, in some embodiments, the belt 111 includes multiple links sequentially connected into a loop; each link includes a connecting shaft 1112 and connecting plates 1111 mounted at both ends of the connecting shaft 1112, and the connecting plates 1111 of adjacent links are connected by rotation. FIGS. 9 and 10 are schematic diagrams illustrating exemplary assembly of links and pressure members according to some embodiments of the present disclosure. In some embodiments, the connecting plate 111 includes an insertion member 1111*a* and an adapter 1111*b*. The insertion members 1111*a* of the two connecting plates 1111 of the rear link are hinged to the adapters 1111*b* of the two connecting plates 1111 of the previous link, respectively, and the multiple links are sequentially connected to form a loop to form the belt 111.

In some embodiments, the pressure member 112 may be a roller, with the roller rotatably attached to the belt 111. As shown in FIG. 9, the roller is rotatably mounted on the connecting shaft 1112 of the link. When the belt 111 rotates to drive the movement of the roller, the friction between the roller and the pressable pipeline 210 may make the roller rotate itself, thus reducing the frictional resistance between the roller and the pressable pipeline 210, reducing the working loss of the roller and the pressable pipeline 210, and improving the service life.

In other embodiments, the pressure member 112 may be a curved pressing plate or a pressing pad with a rounded protrusion. Multiple pressing plates or multiple pressing pads are spaced and fixed to the working plane of the belt 111. For example, the pressing plate or pressing pad is fixed to the connecting shaft 1112 of a single link or between the connecting shafts 1112 of adjacent links. The belt 111 rotates to drive the pressing plate or pressing pad to press the pressable pipeline. The setting of the curved pressing plate and the pressing pad with the rounded protrusion makes the contact part of the pressure member 112 and the pressable pipeline 210 a rounded arc, which may reduce the friction between the pressure member 112 and the pressable pipeline and reduce the working loss of the pressure member 112 and the pressable pipeline 210.

In some embodiments, the surface of the curved pressing plate or the pressing pad with a rounded protrusion may also be provided with a lubrication layer or an anti-wear layer (such as a rubber layer, etc.) to further reduce the friction between the pressure member 112 and the pressable pipeline 210 and enhance the performance of the perfusion system 100.

In some embodiments, the pressure transfer component 110 also includes a driving wheel 113, a driven wheel 114, and a support plate 115. The driving wheel 113 and the driven wheel 114 are the drive wheels of the belt 111. The driven wheel 114 may have 1 or more. For example, as shown in FIG. 3, the pressure transfer component 110 includes a driving wheel 113 and a driven wheel 114, and the spindles of the driving wheel 113 and the driven wheel 114 are rotatably supported on the support plate 115 to form a support structure for the pressure transfer component 110. The belt 111 is set on the driving wheel 113 and the driven wheel 114. In some embodiments, the driving wheel 113 and the driven wheel 114 are sprockets, and the connecting plate 111 of each link has a toothed protrusion 1111c. For example, as shown in FIGS. 3 and 10, the toothed protrusion 1111c of the connecting plate 111 engages with the teeth grooves of the driving wheel 113 and the driven wheel 114 for stable transmission.

In some embodiments, the driving device 120 may employ an electric motor. In other embodiments, the driving device 120 may also employ a fuel engine, steam engine, or other devices that may provide power. In some embodiments, the driving device 120 may be directly connected to the driving wheel 113. In other embodiments, a driving connection may be established between the driving device 120 and the driving wheel 113 by a driving structure, such as a multiple-gear driving connection, etc. The transmission structure is capable of adjusting the rotational speed output by the driving device 120 to the rotational speed required for the operation of the pressure transfer component 110, thereby improving the pressing accuracy of the pressure transfer component 110.

In other embodiments, the belt 111 may be a conveyor belt and the pressure members 112 are fixed to the working plane of the conveyor belt. The driving wheel 113 and the driven wheel 114 may be pulleys that match the conveyor belt. The driving device 120 drives the conveyor belt through the driving wheel 113 to rotate, thereby driving the pressure member 112 to move the pressable pipeline 210.

In other embodiments, the belt 111 may be a chain plate conveyor belt; the pressure member 112 is fixed to the working plane of the chain plate conveyor belt, and the pressure member 112 is mounted on the chain plate to avoid the situation that the pressure member 112 is not firmly fixed when the chain plate is separated at the arc of the two ends of the chain plate conveyor belt. The driving wheel 113 and driven wheel 114 may be sprockets, and the chain plate conveyor belt has a tooth structure similar to the toothed protrusion 1111c of the link shown in FIG. 10 that engages the tooth grooves of the driving wheel 113 and driven wheel 114. The driving device 120 drives the chain plate conveyor belt to rotate through the driving wheel 113, thereby driving the pressure member 112 to move to press the pressable 210.

Referring to FIG. 1, in some embodiments, the perfusion system 100 also includes a support section 130. The pipeline assembly is placed on a pressure-bearing surface 131 of the support section 130, and the pressable section 211 of the pressable pipeline 210 is located between the drive pressing section 110 and the pressure-bearing surface 131. The support section 130 is used to support the pipeline assembly, and the pressure-bearing surface 131 of the support section 130 supports the pressable section 211 of the pressable pipeline 210 in the pipeline assembly, so as to form an effective pressing fit between the pressable section 211 and the drive pressing section 110. As shown in FIG. 1, in the press area, the working plane of the belt 111 and the pressure-bearing surface 131 are positioned opposite and parallel to each other, thus ensuring that the pressure member 112 may continuously press the pressable section 211 placed on the pressure-bearing surface 131 with approximately the same pressure.

In some embodiments, the distance between the pressure transfer component 110 and the support section 130 is adjustable, so the pipeline assembly may be easily replaced and the pressing force of the pressure transfer component 110 on the pipeline assembly may be properly adjusted. Since the pressable section 211 is placed on the pressure-bearing surface 131 of the support section 130 instead of being fixed to the pressure transfer component 110, the perfusion system 100 provided in some embodiments of this present disclosure is easy to use, with simple steps and a wide range of application scenarios. Additional operations of connecting, clamping, or disconnecting the hose are not needed.

In some embodiments, the pressure transfer component 110 and the driving device 120 are fixed to a foundation (not shown in the attached drawings), which may be a wall, shell, bracket, or other structure with a supporting connection, and the support section 130 is connected to the foundation by a lifting mechanism (e.g., hydraulic cylinder, sliding slot, etc.). Therefore, when the support section 130 is raised and lowered by the lifting mechanism, the distance between the pressure transfer component 110 and the pressure-bearing surface 131 may be adjusted to facilitate the overall replacement of the pipeline assembly.

In other embodiments, the support section 130 may be fixed horizontally to a foundation, the driving wheel spindle of the pressure transfer component 110 is supported on the foundation by a bearing, and the driven wheel spindle of the pressure transfer component 110 is mounted on the foundation by an arcuate slide. When lifting or lowering the end of the pressure transfer component 110 near the driven wheel, the distance between the end of the pressure transfer component 110 and the pressure-bearing surface 131 may be adjusted to facilitate the overall replacement of the pipeline assembly.

In some embodiments, the ratio of the horizontal projected area of the press area to the horizontal projected area of the pressure transfer component 110 is greater than 70% when the pressure-bearing surface 131 is horizontal. For example, as shown in FIGS. 1 and 6, the projected area of the pressure transfer component 110 on the pressure-bearing surface 131 is the horizontal projected area of the pressure transfer component 110, a portion of the belt 111 has a flat working plane, and the projected area of this portion of the belt 111 with a flat working plane on the pressure-bearing surface 131 is the horizontal projected area of the press area. The pressure-bearing surfaces 131 located within the press area may all be pressed. In the direction perpendicular to the pressure-bearing surface 131, the space occupied by the pressure transfer component 110 is mainly used for pressing the pumped fluid, therefore, under the premise of pressing the same length of the pressable section 211, the perfusion system 100 provided in some embodiments of this present disclosure may reduce the space occupied by the pipeline assembly by the space for cooperating with pumping, leading to more flexible installation and higher space utilization.

The perfusion system has a wide range of applicable scenarios and a flexible structural design. In some embodiments, the pipeline assembly may be a reservoir bottle plus hose structure. In some embodiments, the pipeline assembly may be provided within a microfluidic chip.

In some embodiments, the pipeline assembly may be provided within the integrated perfusion system 200. The use of the integrated perfusion system 200 makes it possible for the pipeline assembly to be quickly matched to the pressure transfer component 110 for installation and separation for disassembly. In the work, there is no need to connect and clamp the pipeline, or to perform other operations. The pressure transfer component 110 is directly placed at the right position and the integrated perfusion system 200 is pressed. The purpose of the pumping of the fluid may be achieved, which is easy to use.

Figure 11:
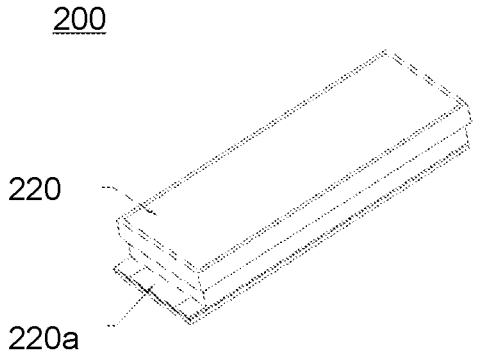
FIG. 11 is a schematic diagram illustrating an exemplary external outline of an integrated perfusion system according to some embodiments of the present disclosure.
Figure 12:
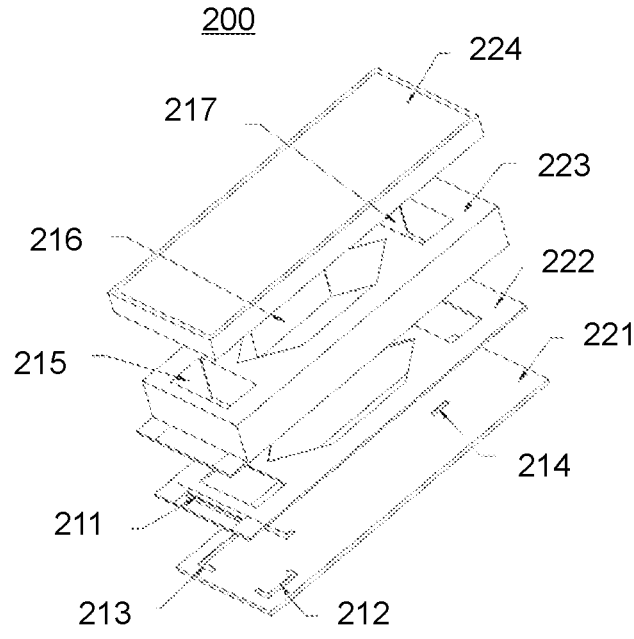
FIG. 12 is a schematic diagram illustrating an exemplary disassembled structure of an integrated perfusion system according to some embodiments of the present disclosure.

Referring to FIGS. 11 and 12, FIG. 11 is a schematic diagram illustrating an exemplary external outline of the integrated perfusion system 200 according to some embodiments of this present disclosure; FIG. 12 is a schematic diagram illustrating an exemplary internal structure of the integrated perfusion system 200 according to some embodiments of the present disclosure. In some embodiments, the integrated perfusion system 200 includes a main body 220. The main body 220 may include a cover 224 and a cassette; the pipeline assembly is set in the cassette, and the cover 224 may close the cassette. For example, as shown in FIG. 12, the cassette may include a first plate body 221, a second plate body 222, and a third plate body 223 that are sequentially sealed and connected from the bottom to the top. Each layer of the plate body may be processed by laser cutting and other means to process each split structure of the pipeline assembly, and then the multi-layer plate body is assembled by gluing and other sealing connections, so that the fine and complex pipeline assembly is integrated in the box.

In some embodiments, the pipeline assembly provided in the cassette includes a liquid storage chamber 215, a liquid storage chamber 216, a waste chamber 217, with the liquid storage chamber 215, the liquid storage chamber 216, and the waste chamber 217 connected in sequence through the pressable pipeline.

In some embodiments, the pressable section 211 of the pipeline assembly may be resilient, so that the pressable section 211 of the pipeline assembly may spring back after the pressure member 112 moves away, thus enabling fluid pumping. For example, the pressable pipeline between the liquid storage chamber 215 and the liquid storage chamber 216 includes a non-pressed section 212, a pressable section 211, and a non-pressed section 213, in sequence, as shown in FIG. 12; the pressable pipeline between the liquid storage chamber 216 and the waste liquid chamber 217 is the non-pressed section 214.

In some embodiments, the pressable section 211 is an embedded tube made of a resilient material, which may be deformed and blocked under the pressure of the pressure transfer component 110, thereby cooperating with the pressure transfer component 110 for fluid pumping. The non-pressed section 212 and the non-pressed section 213 may be embedded tubes made of a rigid material. The non-pressed section 212 and the non-pressed section 213 are not deformed or are only slightly deformed under pressure. The pressable pipeline is provided with two folded parts in the non-pressed section 212 and non-pressed section 213, and the above-mentioned two folded parts are not deformed and blocked when the transmission pressing section 110 presses the pressable pipeline, so that the problem of uneven flow rate may be avoided.

In other embodiments, the pressable section 211 is located in the second plate body 222 and the third plate body 223, the non-pressed section 212 and the non-pressed section 213 are located largely on the first plate body, the height of the pressable section 211 in the box body is higher than the non-pressed section 212 and the non-pressed section 213, the second plate body 222 and the third plate body 223 may be set the pressable section 211 is set as an elastic material plate, and the first plate body 221 is set as a rigid material plate. On the one hand, the above-mentioned setting may prevent the pipeline of the two folded parts from being deformed and blocked by pressure, so as to avoid the problem of uneven flow rate, and on the other hand, it may reduce the resistance of the pressure transfer component 110 when pressing the above-mentioned two folded parts and extend the service life of the pressure transfer component 110.

In some embodiments, the main body 220 has a protrusion component 220a, and the pressable section 211 of the pressable pipeline is provided within the protrusion component 220a. For example, as shown in FIG. 11, the protrusion component 220a is located at the edge of the outer contour of the main body 220. The specific setting position of the protrusion component 220a on the main body 220 may be flexibly adjusted according to the actual application scenario, and the transmission pressing section 11 and the protrusion component 220a may be pressed together to achieve fluid pumping.

Figure 13:
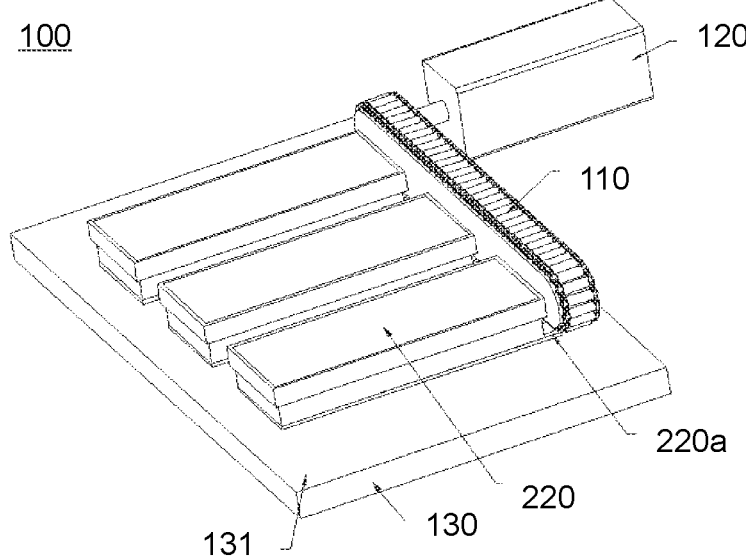
FIG. 13 is a schematic diagram illustrating an exemplary application scenario of an integrated perfusion system in a perfusion system according to some embodiments of the present disclosure.

FIG. 13 is a schematic diagram illustrating an exemplary application scenario of the integrated perfusion system 200 in the perfusion system 100 according to some embodiments of the present disclosure. In some embodiments, the pressure-bearing surface 131 of the support section 130 may carry multiple integrated perfusion systems 200, with a protrusion component 220a of each integrated perfusion system 200 placed between the pressure-bearing surface 131 and the pressure transfer component 110 and cooperating to perform the pressing of the pressable pipeline. As shown in FIG. 13, the multiple integrated perfusion systems 200 are arranged at intervals in a direction parallel to the straight line of movement of the pressure member 112, with the protrusion components 220a of each integrated perfusion system 200 oriented consistently to cooperate with the pressure transfer component 110 for line pressing.

In some embodiments, when the pressure-bearing surface 131 is horizontal, the horizontal projected area of the protrusion component 220a is less than 25% of the horizontal projected area of the main body 220. For example, as shown in FIG. 13, the projected area of the protrusion 220a on the pressure-bearing surface 131 is the horizontal projected area of the protrusion component 220a, and the projected area of the body 220 on the pressure-bearing surface 131 is the horizontal projected area of the main body 220. The protrusion component 220a is located at the edge of the outer contour of the main body 220, and the smaller the proportion of the horizontal projection area of the protrusion 220a to the horizontal projection area of the main body 220, the more space the main body 220 has reserved in the vertical direction for application needs other than pumping fluid. For example, in the case of a restricted volume of the main body 220, the pumping through the protrusion component 220a in conjunction with the pressure transfer component 110 takes up very little vertical space, and the rest of the vertical space of the main body 220 may be used for optical detection.

Some embodiments of the present disclosure also provide a cell cultivation perfusion system 300 comprising a cell incubator and the perfusion system 100 shown in any of the preceding embodiments. In the process of cell cultivation perfusion, not only the accuracy of fluid delivery is required, but also the flow rate of fluid delivery needs to be controlled more precisely. If the flow rate is too fast, it may disperse the cells; if the flow rate is too slow, it may cause the new incoming nutrient fluid to not mix well and uniformly, affecting the absorption efficiency of the cells. The perfusion system 100 provided in some embodiments of this present disclosure is able to precisely control the amount of liquid delivered and the flow rate of liquid delivery, which is easy to regulate. On the other hand, the perfusion system 100 may perform multi-channel fluid delivery with different velocities, which may be suitable for more complex cell cultivation perfusion needs. The perfusion system 100 occupies little space, has a large design space and a high degree of design flexibility, and is especially suitable for high-throughput cell cultivation perfusion under space-limited conditions, which may save a lot of space for the cell cultivation perfusion system 300 and facilitate other subsequent operations, such as optical detection. At the same time, the pressure transfer component 110 in the perfusion system 100 may be quickly separated from the pipeline assembly to facilitate the construction of a high-throughput cell cultivation perfusion system.

The perfusion system 100 at least includes a pressure transfer component 110, a driving device 120, and a pipeline assembly. The pressure transfer component 110, the driving device 120, and the pipeline assembly may be set up in a variety of ways. In some embodiments, the pressure transfer component 110, the driving device 120, and the pipeline assembly are all located within the cell incubator. In some embodiments, a portion of the pipeline assembly is located inside the cell incubator, and the driving device 120, the pressure transfer component 110, and another portion of the pipeline assembly are located outside the cell incubator. In other embodiments, the driving device 120 is provided outside the cell incubator, and the pipeline assembly and at least a portion of the pressure transfer component 110 are provided inside the cell incubator. Specifically, a driving connection is established between the driving device 120 and the pressure transfer component 110, and a portion of the pipeline assembly is provided on the pressure transfer component 110 so that the pressure transfer component 110 presses the pipeline assembly to achieve the delivery of the culture fluid. The driving device 120 (e.g., a motor, a pneumatic machine, etc.) heats up due to continuous operation, thus making it more difficult to control the temperature inside the cell incubator, so it is preferred that the driving device 120 be located outside the cell incubator. If the interconnected driving device and the pressure transfer component are both located outside the cell incubator, it is needed to extend a portion of the pipeline assembly from inside the cell incubator to outside the cell incubator, so that a portion of the pipeline assembly is located on the pressure transfer component to achieve the pressing. In this way, not only the complexity of the pipeline assembly arrangement is increased, but also the possibility of outside gas dissolving in the culture fluid through the wall of the pipeline assembly is increased. By using the perfusion system 100 shown in some embodiments of this present disclosure, at least a portion of the pressure transfer component 110 and the driving device 120 are installed inside and outside the cell incubator, which may improve the efficiency of temperature control in the incubator and reduce the complexity of the pipeline assembly arrangement and avoid contamination of the internal environment of the incubator by the external environment (for example, to avoid contamination of the culture fluid by the dissolution of some external gases through the wall of the pipeline assembly).

It should be noted that different embodiments may produce different beneficial effects, and in different embodiments, the possible beneficial effects may be any one or a combination of the above-mentioned effects, or any other beneficial effect that may be obtained.

The basic concept has been described above. Obviously, for the technicians skilled in the arts, the above-detailed disclosure is only used as an example, and does not constitute a limitation of the present disclosure. Although not explicitly described herein, various modifications, improvements, and corrections to this disclosure may occur to the technicians skilled in the art. Such modifications, improvements, and corrections are suggested in this disclosure and thereof remain within the spirit and scope of the exemplary embodiments of this disclosure.

Meanwhile, the present disclosure uses specific words to describe the embodiments of the present disclosure. For example, "an embodiment," "one embodiment," and/or "some embodiments" means a feature, structure, or characteristic associated with at least one embodiment of this present disclosure. Therefore, it should be emphasized and noted that "one embodiment," "an embodiment" or "an alternative embodiment" mentioned twice or more in different places in this present disclosure does not necessarily refer to the same embodiment. In addition, certain features, structures, or characteristics of one or more embodiments of the present disclosure may be suitably combined.

What is claimed is:

1. A perfusion system, comprising:

a pressure transfer component, the pressure transfer component including a belt and multiple pressure members disposed on the belt at intervals;

a driving device, wherein a driving connection is established between the driving device and the pressure transfer component; and at least one pipeline assembly, the at least one pipeline assembly including at least one pressable pipeline configured for fluid passage;

wherein a press area is formed between the pressure transfer component and each of the at least one pressable pipeline, the multiple pressure members move with the belt, and at least a portion of the multiple pressure members press against the at least one pressable pipeline when moving in the press area;

wherein in the press area, a pressable section of each of the at least one pressable pipeline is simultaneously pressed by adjacent pressure members of the multiple pressure members, thereby forming a blocked fluid section, wherein when the at least one pressable pipeline include multiple pressable pipelines, and the at least a portion of the multiple pressure members press the multiple pressable pipelines within the press area, a length of the blocked fluid section of one or more of the multiple pressable pipelines is greater than a distance between the adjacent pressure members.

2. The perfusion system of claim 1, wherein in the press area, there is only one press position formed through pressing the pressable section of the at least one pressable pipeline by a same pressing member of the multiple pressing members.

3. The perfusion system of claim 1, wherein
  liquid inlet ends of the multiple pressable pipelines being connected to different liquid storage containers, and liquid outlet ends of the multiple pressable pipelines being connected to a same target container; or
  liquid inlet ends of the multiple pressable pipelines being connected to a same liquid storage container, and liquid outlet ends of the multiple pressable pipelines being connected to different target containers.

4. The perfusion system of claim 1, wherein the multiple pressure members move in a straight line in the press area.

5. The perfusion system of claim 4, wherein the at least one pressable pipeline includes multiple pressable pipelines, and pressable sections of the multiple pressable pipelines of the at least one pipeline assembly are disposed at intervals along the straight line of a movement of the multiple pressure members.

6. The perfusion system of claim 4, wherein when the at least one pressable pipeline includes multiple pressable pipelines:
  pressable sections of the multiple pressable pipelines are disposed side by side in a direction that is perpendicular to the straight line of the movement of the multiple pressure members and parallel to a working plane of the belt in the press area.

7. The perfusion system of claim 4, wherein a pressable section of one or more of the at least one pressable pipeline is a straight-line section, a folded-line section, or a curved section.

8. The perfusion system of claim 7, wherein when the pressable section is the straight-line section, the straight-line section is arranged such that an angle between the straight-line section and the straight line of a movement of the multiple pressure members ranges from 0~89°.

9. The perfusion system of claim 7, wherein
  the blocked fluid section moves with a movement of the pressure members, a length of an initial blocked fluid section being less than or equal to a length of a moved blocked fluid section.

10. The perfusion system of claim 1, wherein the perfusion system further includes a support section, the at least one pipeline assembly being placed on a pressure-bearing surface of the support section, wherein the pressable section of each of the at least one pressable pipeline is located between the pressure-bearing surface and the pressure transfer component.

11. The perfusion system of claim 10, wherein when the pressure-bearing surface is horizontal, a ratio of a horizontal projected area of the press area to a horizontal projected area of the pressure transfer component is greater than 70%.

12. The perfusion system of claim 10, wherein the perfusion system is an integrated perfusion system, wherein
  the integrated perfusion system includes a main body, the main body having a protrusion component,
  the pressable section of each of the at least one pressable pipeline is provided within the protrusion component, wherein the protrusion component is placed between the pressure-bearing surface and the pressure transfer component, and the protrusion component is configured to cooperate in pressing the at least one pressable pipeline.

13. The perfusion system of claim 12, wherein when the pressure-bearing surface is horizontal, a ratio of a horizontal projected area of the protrusion component to a horizontal projected area of the main body is less than 25%.

14. The perfusion system of claim 1, wherein in the press area, at least two of the multiple pressure members simultaneously press on each of the at least one pressable pipeline.

15. The perfusion system of claim 1, wherein the multiple pressure members on the belt are equally spaced from each other;
  a distance between adjacent pressure members of the multiple pressure members is 0.5-100 mm.

16. The perfusion system of claim 1, wherein the belt includes multiple links sequentially connected in a loop, wherein
  each of the multiple links includes a connecting shaft and a connecting plate installed at both ends of the connecting shaft, the connecting plates of adjacent links being rotatably connected.

17. The perfusion system of claim 1, wherein the at least one pressable pipeline includes at least one diameter-varying section, wherein for each of the at least one diameter-varying section, a cross-sectional area of the diameter-varying section varies.

18. The perfusion system of claim 8, wherein when distances between adjacent pressure members of the multiple pressure members are equal, velocities of the pressure members are equal, and a cross-sectional area of the at least one pressable pipeline is invariable,
  the plane where the straight-line section is located is parallel to a working plane of the belt in the press area, a pumping speed of the straight-line section when the straight-line section is parallel to the straight line of a movement of the multiple pressure members is less than a pumping speed of the straight-line section when there is an acute angle between the straight-line section and the straight line of the movement of the multiple pressure members.

19. A cell perfusion cultivation system, comprising a cell incubator, wherein the cell incubator is provided with a perfusion system, the perfusion system including:
  a pressure transfer component, the pressure transfer component including a belt and multiple pressure members disposed on the belt at intervals;
  a driving device, wherein a driving connection is established between the driving device and the pressure transfer component; and
  at least one pipeline assembly, the at least one pipeline assembly including at least one pressable pipeline configured for fluid passage;
  wherein a press area is formed between the pressure transfer component and each of the at least one pressable pipeline,
  the multiple pressure members move with the belt, and
  at least a portion of the multiple pressure members press against the at least one pressable pipeline when moving in the press area;
  wherein in the press area, a pressable section of each of the at least one pressable pipeline is simultaneously pressed by adjacent pressure members of the multiple pressure members, thereby forming a blocked fluid section, wherein
  when the at least one pressable pipeline include multiple pressable pipelines, and the at least a portion of the multiple pressure members press the multiple pressable pipelines within the press area, a length of the blocked fluid section of one or more of the multiple pressable pipelines is greater than a distance between the adjacent pressure members.

\* \* \* \* \*